US00PP22948P3

(12) United States Plant Patent
Austin

(10) Patent No.: US PP22,948 P3
(45) Date of Patent: Aug. 14, 2012

(54) ***ROSA HYBRIDA* SHRUB PLANT NAMED 'AUSLOUNGE'**

(50) Latin Name: *Rosa hybrida*
Varietal Denomination: AUSlounge

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 21 days.

(21) Appl. No.: 13/065,159

(22) Filed: Mar. 14, 2011

(65) Prior Publication Data

US 2012/0096605 P1 Apr. 19, 2012

(30) Foreign Application Priority Data

Oct. 13, 2010 (QZ) ..... PRB 2010/2156

(51) Int. Cl.
*A01H 5/00* (2006.01)

(52) U.S. Cl. ..... Plt./107; Plt./102

(58) Field of Classification Search ..... Plt./102, Plt./107
See application file for complete search history.

*Primary Examiner* — Susan McCormick Ewoldt
(74) *Attorney, Agent, or Firm* — Kauth, Pomeroy, Peck & Bailey LLP

(57) ABSTRACT

A variety of rose plant of the shrub class, named 'AUSlounge'. The 'AUSlounge' rose is a plant suitable for repeat flowering production having flowers that are of medium size, tough and reliable, and have a deep glowing pink. In addition, the flowers are shallowly cupped at first, but as they age the outer petals reflex back and reveal a button eye.

1 Drawing Sheet

Classification: The present invention relates to a new *Rosa hybrida* shrub.

Variety denomination: The new plant has the varietal denomination 'AUSlounge.'

CROSS-REFERENCE TO RELATED APPLICATIONS

The current application claims priority to a European Community Plant Variety Application No. 2010/2156, filed Oct. 13, 2010, the disclosure of which is incorporated herein by reference.

ORIGIN OF INVENTION

This invention relates to a new and distinct variety of shrub rose plant named 'AUSlounge', which was originated by crossing two unnamed, unpatented varieties of *Rosa hybrida*.

BACKGROUND OF THE INVENTION

The primary objective of this breeding was to produce a tough and reliable variety of rose of medium size, with flowers of deep glowing pink, that are healthy, weather-resistant, and which forms an attractive bushy shrub. The flowers are shallowly cupped at first and as they age the outer petals reflex back and reveal a button eye.

SUMMARY OF THE INVENTION

Among the features which distinguish the new variety from other presently available and commercial rose cultivars known to the inventor is the following combination of characteristics: the flower is particularly weather resistant, and has blooms that even in periods of continual rain do not ball and have petals that drop cleanly; blooms that are shallowcupped and deep pink that open out to reveal a button eye; and having a fine, strong fragrance that is warm and spicy with a classic Old Rose character.

Asexual reproduction of the new variety by budding as performed outdoors at Bowling Green Lane in Albrighton, Britain shows that the foregoing and other distinguishing characteristics come true to form and are established and transmitted through succeeding asexual propagations. 'AUSlounge' may be asexually propagated by budding. The budding successfully occurred on the plant/rootstock *Rosa* cv. 'Dr. Huey' in the United States, and *Rosa dumetorum* cv. 'Laxa' for the observed plants in the UK.

COMPARISON WITH PARENTS

The new rose may be distinguished from its seed parent, by the following combination of characteristics: whereas the seed parent is more disease prone, not vigorous and light pink, 'AUSlounge' is vigorously disease resistant and vigorous growth with deep pink flowers.

The new variety may be distinguished from its pollen parent, by the following combination of characteristics: whereas the pollen parent is of a buff pink color and a spreading growth, 'AUSlounge' is a bushy shrub with a deep pink color.

COMPARISON WITH THE CLOSEST COMMERCIALLY AVAILABLE CULTIVAR

The closest commercially available cultivar to the new variety is the 'AUSkitchen' (co-pending application Ser. No. 13/065,165). The new rose may be distinguished from the 'AUSkitchen' variety by the following combination of characteristics: the 'AUSlounge' produces blooms that are generally smaller with fewer petals than 'AUSkitchen.' More particularly, the way in which the blooms are held on the plant differs. On 'AUSlounge' the blooms are held in small, flatter clusters of 4 to 6 blooms and on 'AUSkitchen' they are held in larger pyramidal clusters of 10 to 14 blooms. In addition, 'AUSlounge' grows into a larger shrub than 'AUSkitchen' and the foliage of 'AUSkitchen' is glossier than that of 'AUSlounge.'

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown outdoors in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2 cm long and 1.6 cm in diameter when the petals start to unfurl.

*Form*.—The bud form is pointed ovoid.

*Color*.—When sepals first divide, the bud color is red-purple RHS N57B. When half blown, the upper sides of the petals are red-purple RHS N57B, and the lower sides of the petals are red-purple RHS N57C.

*Calyx*.—Shape: star-shape, folded back. Length: 7.5 cm. Diameter: 7.5 cm.

*Sepals*.—Arrangement: Regular, opening to a star shape. Color: Upper Surface: green RHS 138B with red-purple RHS 58A. Lower Surface: green RHS 138B with red-purple RHS 58A. Length: 3.3 cm. Width: 8 mm. Shape: Lanceolate. Margin: Hairy edges. Surface texture: Upper Surface: Slightly downy. Lower Surface: Smooth. Number: There are 5 unappendaged sepals with hairy edges.

*Receptacles*.—Color: green RHS 138B with red-purple RHS 58A. Shape: apple. Size: small, about 0.8 cm×0.7 cm. Surface: Smooth.

*Peduncle*.—Length: short, averaging about 7 cm. Surface: Smooth. Color: green RHS 138B with some red-purple RHS 58A. Strength: Normal.

Blooms:

*Size*.—Medium, average open diameter is about 7.5 cm.

*Borne*.—Several together in small clusters of 4 to 5 blooms having flat shape.

*Stems*.—Strength: Normal, average length is about 7 cm. Diameter: 2.5 mm.

*Form*.—When first open, bloom is cupped. Permanence of bloom: flattens and outer petals curl back.

Petalage: Number of petals under normal conditions: 42.

*Color*.—The upper sides of the petals are red-purple RHS N57C. The reverse sides of the petals are red-purple RHS N57D, and a yellow spot RHS 8D on both sides.

*Variegations*.—N/A.

*Discoloration*.—The general tonality at the end of the first day is red-purple RHS N57C, and at the end of the third day is the same. Thereafter color fades slightly from RHS N57C to RHS N57D.

*Fragrance*.—Strong. Character of fragrance: Spicy.

Petals:

*Texture*.—Thin.

*Size*.—Width: 3.3 mm. Length: 3.8 mm.

*Surface*.—Smooth.

*Shape*.—Deltoid.

*Margin*.—Some entire and some notched.

*Apex shape*.—Rounded with some notched.

*Base shape*.—Obcordate.

*Form*.—Incurved.

*Arrangement*.—Imbricated.

*Petaloids*.—Number: About 7. Color: red-purple RHS N57C. Length: 12 mm. Width: 3 mm. Shape: Half-moon. Margin: Irregular.

*Persistence*.—Petals drop off cleanly before drying.

*Lastingness*.—On the plant: Fair, about 5 days. As a cut flower: Not tested.

Reproductive parts:

*Stamens*.—Number: 60. Length: 6 mm.

*Anthers*.—Length: 3 mm. Color: yellow-orange RHS 15C. Arrangement: Regular around styles, tucked in calyx or partly so and mixed with petaloids.

*Filaments*.—Color: yellow-orange RHS 15D. Length: 4 mm.

*Pollen*.—Color: yellow-orange RHS 15C.

*Pistils*.—Number: 60. Length: 4.5 mm.

*Styles*.—Color: white RHS 155C. Length: 3 mm.

*Stigmas*.—Color: greyed-orange RHS 163B with red-purple RHS 60C. Length: 1.5 mm.

*Hips*.—None Observed.

PLANT CHARACTERISTICS

Plant form: Shrub, compact and bushy.

Plant growth: Branching.

Age to maturity: Two years.

Mature plant: Height: 120 cm. Width: 90 cm.

Rootstock: *Rosa* cv. 'Dr. Huey' in the United States, *Rosa dumetorum* cv. 'Laxa' for the observed plants in the UK.

Foliage:

*Number*.—Leaflets on normal mid-stem leaves is: 5 (including terminal leaflet).

*Size*.—Small, about 12 cm long×7 cm wide.

*Quantity*.—Abundant. Number of leaves per flowering stem is: 10.

*Color*.—New foliage: Upper side: yellow-green RHS 144A tinged with greyed-orange RHS 176A. Lower side: yellow-green RHS 144A tinged with greyed-orange RHS 176A. Old foliage: Upper side: green RHS 139A. Lower side: green RHS 137A.

Leaflets:

*Size*.—About 4.3 cm long×3.2 cm wide.

*Shape*.—Broadly oval.

*Base shape*.—Some rounded and some cordate.

*Apex shape*.—Acuminate (slightly).

*Texture*.—Leathery.
*Edge*.—Serrated.
*Serrations*.—Single.
*Petiole*.—Color: green RHS 143B with some red-purple RHS 60A. Length: 3.5 cm. Width: 1.2 mm. Surface Texture: Smooth.
*Petiole rachis*.—Color: green RHS 143B, with some red-purple RHS 60A. Underside: with prickles.
*Stipules*.—Length: 2.3 cm, serrated. Color: green RHS 143A.
*Auricle*.—Shape: Triangular, broad. Length: 10 mm. Width: 4 to 5 mm at widest point. Color: green RHS 143A.
*Vein color*.—Same as leaf color.
*Venation pattern*.—Reticulate.

Wood:
*New wood*.—Color: greyed-orange RHS 176A. Bark: Smooth.
*Old wood*.—Color: green RHS 143A. Bark: Smooth.

Branching habit:
*Number*.—7.
*Lateral branch dimensions*.—Length: 45 cm. Width: 5 mm.

Stems:
*Mature stem*.—Length: 50 cm. Diameter: 6 mm.
*Internode distance*.—7 cm. The above measurements are all variable, depending on growing conditions in a season
*Stem pubescence present*.—No. .

Prickles:
*Quantity*.—On main canes from base: Ordinary. Number per stem length: 15 per 10 cm. On laterals from main canes: Ordinary. Number per stem length: 15 per 10 cm.
*Form*.—Deep concave and some linear.
*Length*.—4 mm.
*Color when young*.—Red-purple RHS 58A.
*Color when mature*.—Greyed-orange RHS 176B.

Small prickles:
*Quantity*.—Main stalk: Many. Number per stem length: 25 per 10 cm. Laterals: Many. Number per stem length: 20 per 10 cm.
*Color*.—When young: red-purple RHS 58A. When mature: greyed-orange RHS 176B.

Disease resistance:
*Mildew*.—Resistant.
*Blackspot*.—Resistant.
*Rust*.—Resistant.

Pest resistance: Not tested.
Winter hardiness: Not tested.
Growing conditions: Normal.

What is claimed is:

1. A new and distinct variety of rose plant of the shrub class suitable for repeat flower production, substantially as herein shown and described.

* * * * *

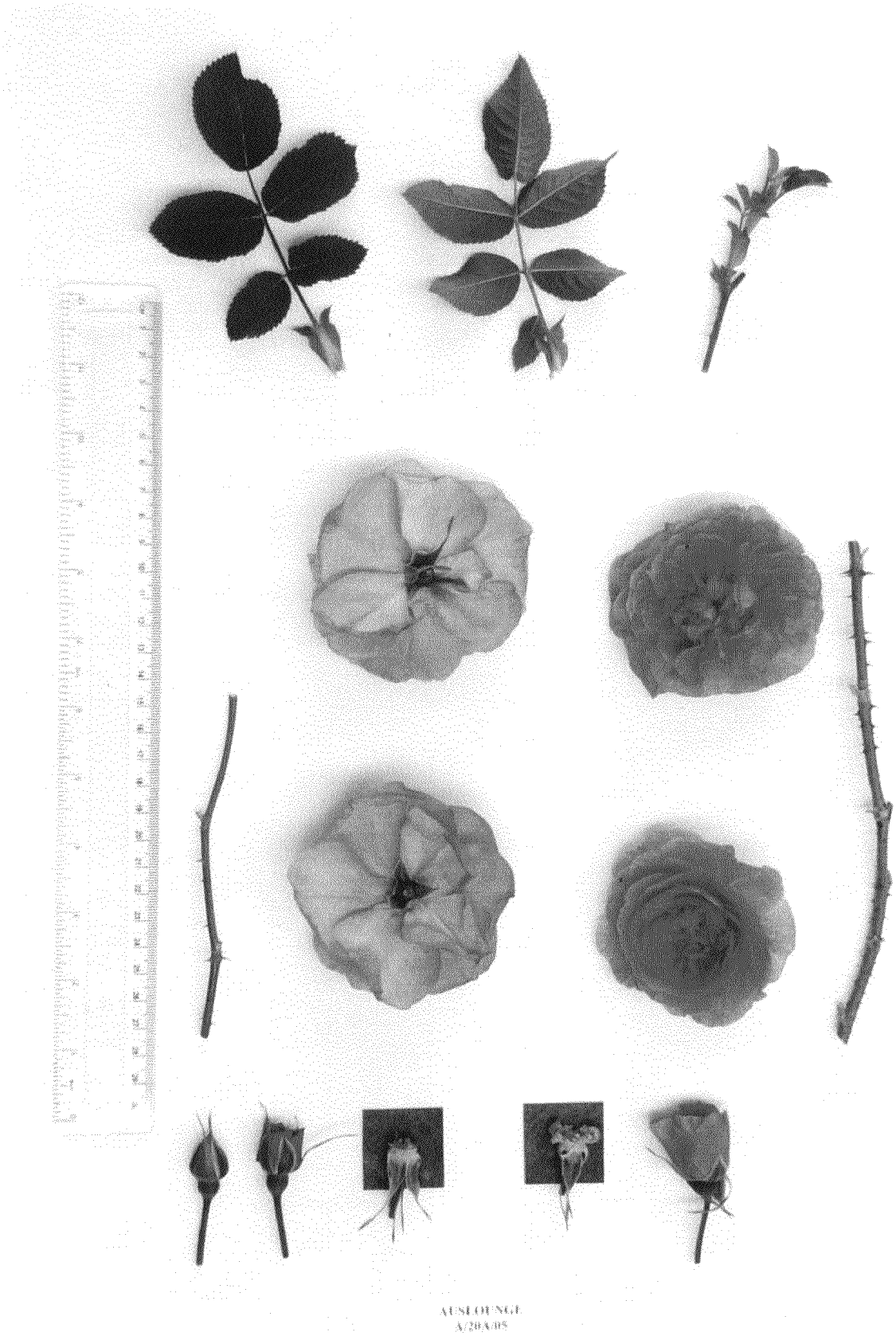
AUSLOUNGE
A/28A/08